(12) United States Patent
Williams

(10) Patent No.: US 6,286,455 B1
(45) Date of Patent: *Sep. 11, 2001

(54) AUTOMATED IN OVO INJECTION APPARATUS

(75) Inventor: Christopher J. Williams, Apex, NC (US)

(73) Assignee: Embrex, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/484,824

(22) Filed: Jan. 17, 2000

Related U.S. Application Data

(63) Continuation of application No. 09/225,933, filed on Jan. 6, 1999, now Pat. No. 6,032,612.
(60) Provisional application No. 60/071,221, filed on Jan. 12, 1998.

(51) Int. Cl.$^7$ .................................................. A01K 45/00
(52) U.S. Cl. ............................................................. 119/6.8
(58) Field of Search ........................... 119/6.5, 6.6, 6.7, 119/6.8

(56) References Cited

U.S. PATENT DOCUMENTS

| | | | |
|---|---|---|---|
| Re. 35,973 | 12/1998 | Paul et al. | 119/6.8 |
| 2,477,752 | 8/1949 | Kiss | 119/6.8 |
| 3,552,394 | 1/1971 | Horn | 128/218 |
| 4,458,630 | 7/1984 | Sharma et al. | 119/1 |
| 4,512,768 | 4/1985 | Rangaswamy | 604/191 |
| 4,593,646 | 6/1986 | Miller et al. | 119/1 |
| 4,681,063 | 7/1987 | Hebrank | 119/1 |
| 4,903,635 | 2/1990 | Hebrank | 119/1 |
| 5,056,464 | 10/1991 | Lewis | 119/6.8 |
| 5,136,979 | 8/1992 | Paul et al. | 119/6.8 |
| 5,158,038 | 10/1992 | Sheeks et al. | 119/6.8 |
| 5,176,101 | 1/1993 | Paul et al. | 119/6.8 |
| 5,339,766 | 8/1994 | Phelps et al. | 119/6.8 |
| 5,438,954 | 8/1995 | Phelps et al. | 119/6.8 |
| 5,745,228 | 4/1998 | Hebrank et al. | 356/53 |
| 5,784,992 | 7/1998 | Petitte et al. | 119/6.8 |
| 6,032,612 | * 3/2000 | Williams | 119/6.8 |

* cited by examiner

Primary Examiner—Thomas Price
(74) Attorney, Agent, or Firm—Myers Bigel Sibley & Sajovec

(57) ABSTRACT

A multi-site in ovo injection apparatus and related methods for treating live eggs is disclosed. The multi-site injection apparatus includes one or more injection delivery devices which are configured to deliver multiple treatment substances to predetermined areas of eggs. The treatment substances can be provided so that they are spatially and/or temporally separate. The devices and methods enable the effective use of a plurality of treatment substances even those that are effective when used alone but can be noxious if mixed.

40 Claims, 6 Drawing Sheets

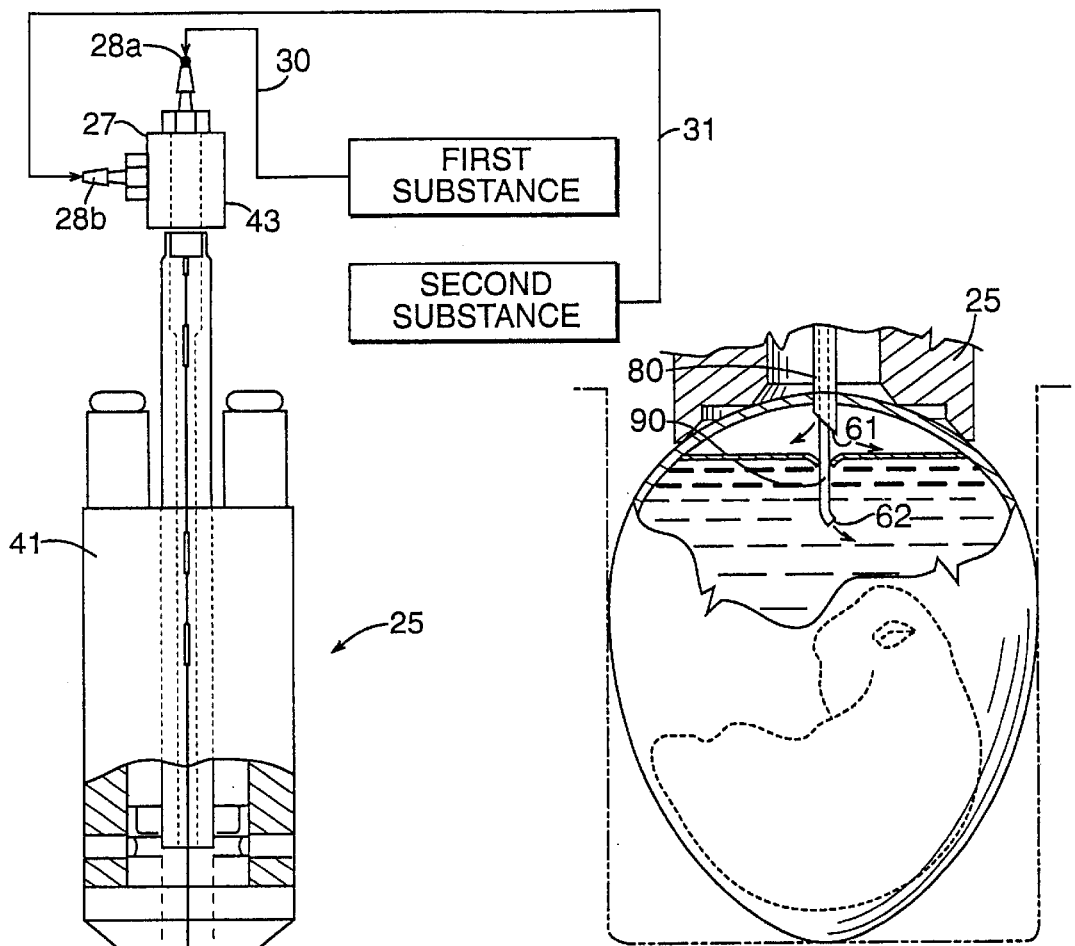
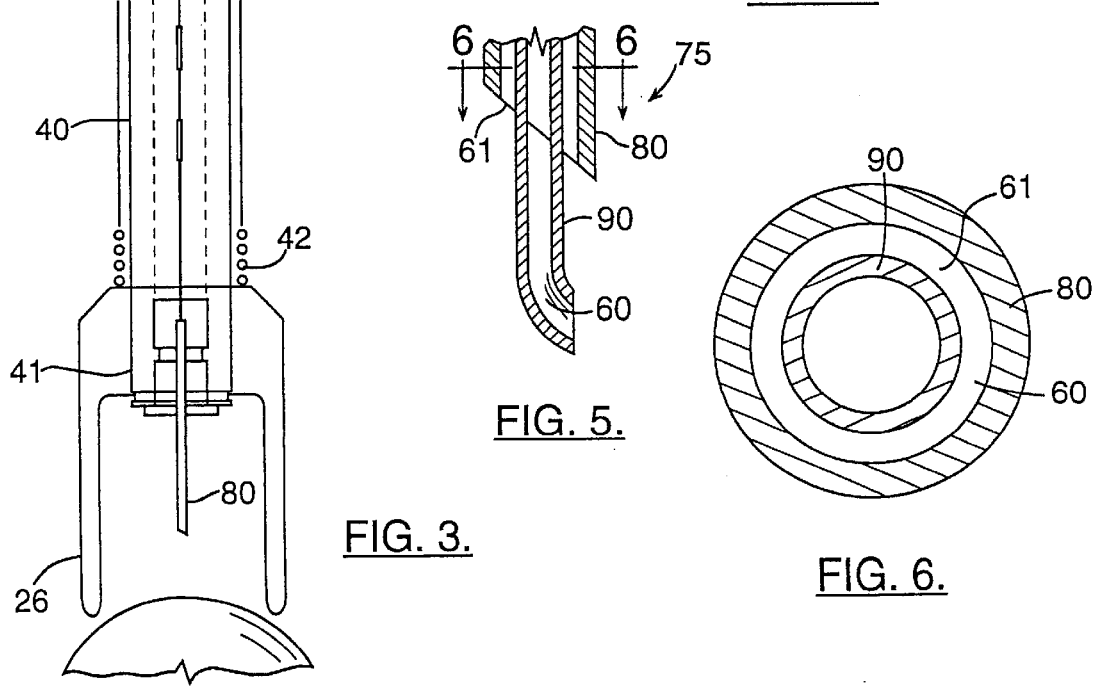
FIG. 3.
FIG. 4.
FIG. 5.
FIG. 6.

AUTOMATED IN OVO INJECTION APPARATUS

RELATED APPLICATIONS

This application is a continuation of copending U.S. patent application Ser. No. 09/225,933, filed on Jan. 6, 1999 U.S. Pat. No. 6,032,612 which claims the benefit of Provisional No. 60/071,221 filed Jan. 12, 1998.

FIELD OF THE INVENTION

The present invention relates to treatment of avian embryos and, more particularly, relates to in ovo injection devices and methods for delivering various substances to live embryonated eggs.

BACKGROUND OF THE INVENTION

Injections of various substances into avian eggs have been employed to decrease post-hatch mortality rates, increase the potential growth rates or eventual size of the resulting chicken, and even to influence the gender determination of the embryo. Similarly, injections of antigens into live eggs have been employed to incubate various substances used in vaccines which have human or animal medicinal or diagnostic applications.

Examples of substances which have been proposed as viable treatment (or harvestable vaccine material) alternatives for delivery via in ovo injection of avian embryos include live culture vaccines, antibiotics, vitamins, and even competitive exclusion media (a live replicating organism). Specific examples of treatment substances are described in U.S. Pat. No. 4,458,630 to Sharma et al, and U.S. Pat. No. 5,028,421 to Fredericksen et al.

Conventionally, the physical injection has been typically targeted at preferred positions within the egg in order to administer the substance into specific developing regions of the embryo. As understood by those of skill in the art, as the incubation period progresses towards maturity (i.e., hatching), the embryo and its membranes, e.g., the air cell, the allantois, and yolk sac, correspondingly change in both volume and position within the egg shell. Additionally, the quantitative volume of the enclosed fluids vary as well; for example, the density of the allantois (fluid, solid) varies as a function of time over the incubation period.

Thus, selection of both the site and time of treatment can impact the effectiveness of the injected substance as well as the mortality rate of the treated embryos. See e.g., U.S. Pat. No. 4,458,630 to Sharma et al., U.S. Pat. No. 4,681,063 to Hebrank, and U.S. Pat. No. 5,158,038 to Sheeks et al.

SUMMARY OF THE INVENTION

The present invention, recognizes that there is a need to introduce multiple substances into a live egg with a minimum of trauma thereto, including substances which are effective treatment alternatives when separately injected but become biologically noxious when combined. Thus, a first object of the present invention is to provide a multi-site in ovo injection device for delivering a variety of treatment substances to avian embryos while minimizing the risk of injury thereto.

Additionally, the present invention recognizes that there is a need to withdraw multiple samples from a live egg with a minimum of trauma thereto, including withdrawing two samples from different compartments of, or locations in, the egg at the same time. Thus, a further object of the present invention is to provide a multi-site in ovo sampling device for withdrawing a variety of samples from avian embryos while minimizing the risk of injury thereto.

It is another object of the present invention to introduce, without mixing, biologically incompatible products in ovo to embryos.

It is a further object of the present invention to separately introduce without mixing at least two different treatment materials into different locations in the egg, through either a single or two separate delivery paths.

It is another object of the present invention to introduce at least two different treatment substances which are separately delivered by one or more of time and spatial separation into an opening in the egg shell.

These and other objects, advantages, and features are provided by a multi-site or multi-dosage injection or withdrawal methods and apparatus disclosed herein. The methods and apparatus of the invention deliver at least two different substances into predetermined areas within the egg, or withdraw samples from at least two different predetermined locations in the egg.

In particular, a first aspect of the present invention is a multi-injection method for treating avian embryos in ovo. In the method, an avian egg is oriented into a predetermined position and a small first opening is introduced into the shell of the avian egg. A delivery device which has either a single or a plurality of lumens therein is extended through the first opening and into the egg a predetermined depth. Predetermined dosages of a first substance and a second substance are separately released into the egg and the delivery device is retracted from the egg, thereby treating the avian embryo. Advantageously, a plurality of lumens can include separate needles that separately deliver the first and second substances to spatially separate areas, or different compartments, of the egg. In one embodiment, a first needle extends longitudinally a greater distance in the egg than a second needle; alternatively, one or more of the needles can include a side port to dispense the substance transversely spatially separated from the other substance. Alternatively, the needles can be adapted to withdraw a sample of material from the egg.

Another aspect of the present invention includes a multi-injection method for treating avian embryos in ovo that first orients an avian egg into a predetermined position and then introduces a small first opening into the shell of an avian egg. Additionally, a small second opening is introduced into the shell of the avian egg, the second opening being spaced apart from the first opening. Respective ones of the first and second delivery devices are extended through corresponding first and second openings and into the egg a predetermined depth. A predetermined dosage of a first substance and a second substance is released from respective ones of the first and second delivery devices into the egg. The delivery devices are retracted from the egg, thereby treating the avian embryo. Alternatively, the delivery devices can be adapted as sampling devices, to withdraw a sample of material from the egg.

Yet another aspect of the present invention includes a multi-injection method for treating avian embryos in ovo which orients an avian egg into a predetermined position and introduces a small first opening into the shell of an avian egg. A delivery device is extended through the first opening and into the egg a predetermined depth. Predetermined dosages of a first substance and a second substance are released into the egg and the delivery device is retracted from the egg, thereby treating the avian embryo. Advantageously, this method temporally combines the different substances to minimize degradation of the substances attributed to reactance therebetween. Thus, preferably, this method allows the first and second substances to be stored in separate chambers and temporally combines or mixes the first and second substances, either with an active mixing chamber, or by introducing them into a common delivery path, prior to delivery into the egg.

An additional aspect of the present invention is directed towards an automated in ovo injection apparatus. The apparatus comprises a fixture for holding a plurality of eggs in a substantially upright and aligned position. The fixture is configured to provide external access to predetermined areas of the eggs. The apparatus also includes a plurality of injection delivery devices configured to contact predetermined areas of the egg; at least one of the injection devices corresponds to each egg in the fixture. Each of the delivery devices comprises a first and second lumen that is adapted to be received into the egg. The apparatus further comprises a first treatment substance container for holding a first treatment substance. The first container is in fluid communication with each of the plurality of injection delivery devices. The apparatus also includes a second treatment substance container for holding a second treatment substance. The second container is in fluid communication with each of the plurality of injection devices. The first container and each of the plurality of injection devices defines a first fluid pathway therebetween. Similarly, the second container and each of the plurality of injection devices define a second fluid pathway therebetween. A pump is operably associated with the first and second containers and the injection units for delivering a predetermined dosage of each of the first and second treatment substances to each of the injection devices. Alternatively, the delivery devices can be adapted to withdraw a sample of material from the egg, where the samples are maintained in separate fluid pathways.

Advantageously, various alternative embodiments of the injection and sampling delivery devices allow for a multiplicity of convenient and useful configurations. For example, the double lumens can be concentrically configured to be telescopically extended at different positions into the egg. Alternatively, the first and second lumens can be provided by a plurality of needles of differing configurations, such as length, port position, and the like.

Another aspect of the present invention is also directed to an automated in ovo injection or sampling apparatus. The apparatus comprises a fixture for holding a plurality of eggs in an aligned position, such that the fixture is configured to provide external access to predetermined areas of the eggs. The apparatus includes a plurality of first injection delivery (or sampling) devices and a plurality of second injection delivery (or sampling) devices, each configured to contact predetermined areas of the egg, a respective one of each of the first and second injection delivery (or sampling) devices corresponding to one egg in the fixture. The device also includes first and second treatment substance containers for holding respective ones of first and second treatment substances (or first and second sample substance containers for holding respective ones of first and second samples withdrawn from the egg). The first container is in fluid communication with each of the first injection delivery devices and the second container is in fluid communication with each of the second injection delivery devices. Thus, the first container and each of the first delivery devices define a first fluid pathway therebetween and the second container and each of the second injection delivery devices define a second fluid pathway therebetween such that the first pathway is separate from the second pathway. A pump is operably associated with the first and second containers for delivering a predetermined dosage of each of the first and second treatment substances to each of the respective first and second injection devices. Similar to the apparatus above, this device can be alternatively configured to deliver different treatment substances to (or withdraw different samples from) different treatment sites within the egg.

Eggs treated by the method of the present invention are preferably incubated to hatch after the treatment substances are administered.

The foregoing and other objects and aspects of the present invention are explained in detail in the specification set forth below.

BRIEF DESCRIPTION OF THE DRAWINGS

FIG. 3 is an enlarged section view taken along line 3—3 in FIG. 2 illustrating one embodiment of a multi-site injection head according to the present invention.

FIG. 4 is an enlarged view of the injection head in FIG. 3 with lumens shown downwardly extended and delivering substances into an egg, according to one embodiment of the present invention.

FIG. 5 is an enlarged sectional view of the lumens shown in FIG. 4.

FIG. 6 is an end view taken along lines 6—6 in FIG. 5.

DETAILED DESCRIPTION OF THE PREFERRED EMBODIMENTS

Figure 1:
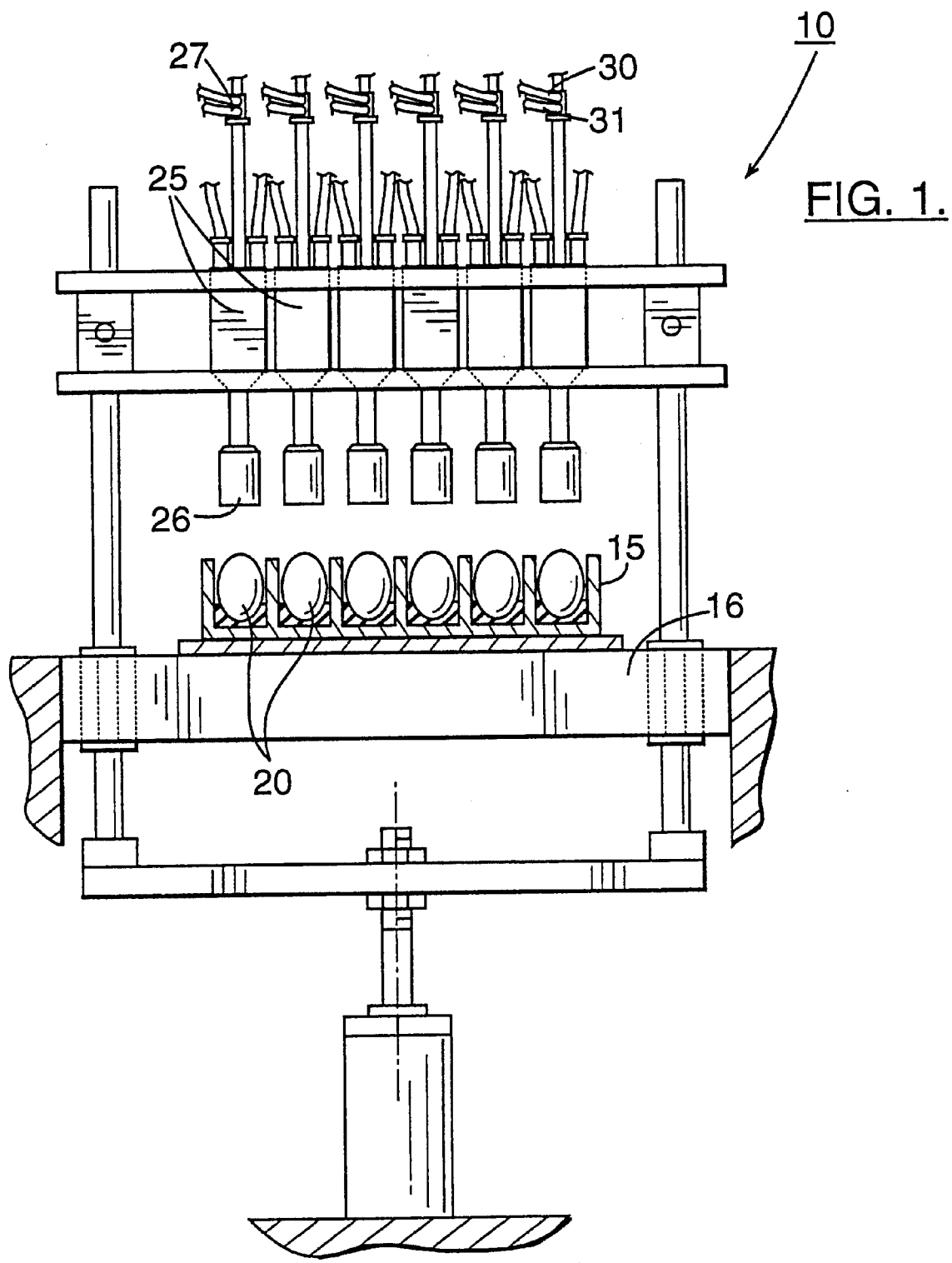
FIG. 1 is a partial front view of a multi-site injection apparatus according to the present invention.
Figure 2:
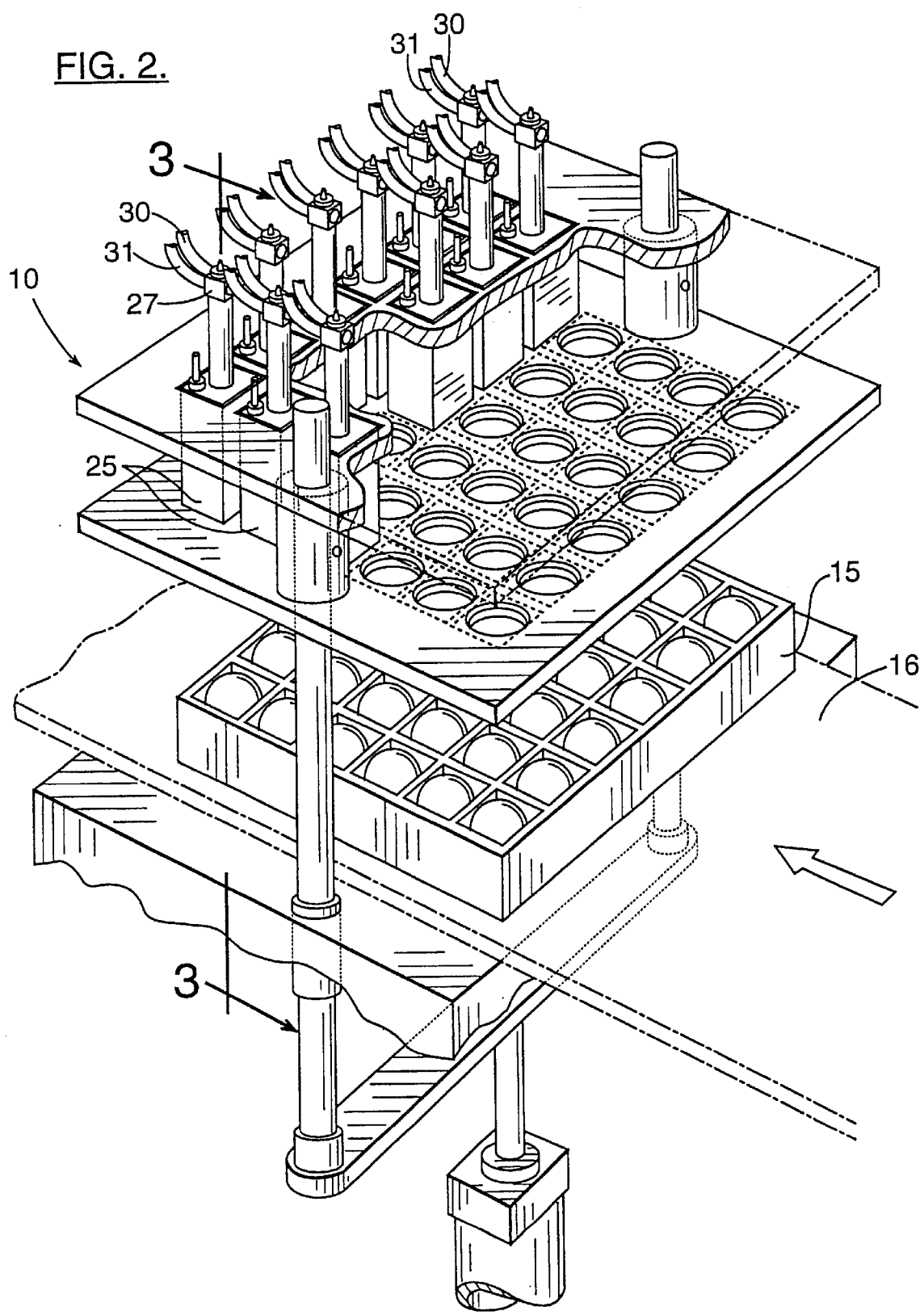
FIG. 2 is side perspective view of a multi-site injection apparatus shown in FIG. 1.

The present invention is practiced with eggs, particularly bird or avian eggs such as chicken, turkey, duck, geese, quail, pheasant, or ostrich eggs. The eggs are viable eggs; that is, eggs containing a live avian embryo. The eggs may be in any stage of embryonic development, including both early embryonic development and late embryonic development.

The present invention will now be described more fully hereinafter with reference to the accompanying drawings, in which a preferred embodiment of the invention is shown. This invention may, however, be embodied in many different forms and should not be construed as limited to the embodiments set forth herein. Rather, these embodiments are provided so that this disclosure will be thorough and complete and will fully convey the scope of the invention to those skilled in the art.

In the drawings, the thickness of layers and regions are exaggerated for clarity. Like numbers refer to like elements throughout.

In the description of the present invention that follows, certain terms are employed to refer to the positional relationship of certain structures relative to other structures. As used herein, the term "longitudinal" and derivatives thereof refer to the general direction defined by the longitudinal axis of the egg that extends upwardly and downwardly between opposing top and bottom ends of the egg. As used herein, the terms "outer", "outward", "lateral" and derivatives thereof refer to the direction defined by a vector originating at the longitudinal axis of the egg and extending horizontally and perpendicularly thereto. Conversely, the terms "inner", "inward", and derivatives thereof refer to the direction opposite that of the outward direction. Together the "inward" and "outward" directions comprise the "transverse" direction.

The present invention employs a single (FIG. 1) or multiple head (FIG. 10) injection device to introduce treatment substances into the egg such that the egg benefits from multiple treatment substances. As such the apparatus is preferably configured to automatically introduce (in one or more of a spatially and temporally separated sequence) multiple substances into a live egg with a minimum of trauma thereto. Advantageously, this apparatus can deliver substances that are effective treatment alternatives when separately injected but become less effective or biologically noxious when combined.

It will be apparent to one of ordinary skill in the art that the apparatus described herein for injection substances into eggs can be adapted to withdraw samples from avian eggs. Withdrawal of such samples may be required for any variety of reasons, such as to monitor the health of the embryo or assess the status of the egg. Withdrawing a fluid sample from avian eggs to determine gender of the avian embryo is described in PCT Application No. PCT/US97/18251 (published as WO 98/14781 on Apr. 9, 1998, the disclosure of which is incorporated herein in its entirety). As used herein, an "injection delivery device", "delivery device" or "injection needle" encompasses the use of the devices for the withdrawal of samples from avian eggs. Similarly, the injection apparatus described herein may also be termed "sample withdrawal apparatus".

Referring now to the drawings, FIG. 1 illustrates one embodiment of an automated multi-site injection apparatus 10 according to the present invention. As shown, the apparatus 10 includes a flat 15, a stationary base 16, and a plurality of injection delivery devices 25 with fluid delivery means such as lumens or needle(s) 90 positioned therein. The flat 15 holds a plurality of eggs 20 in a substantially upright and aligned position. The flat 15 is configured to provide external access to predetermined areas of the eggs 20. The egg is held in by the flat 15 so that a respective one egg is in proper alignment relative to a corresponding one of the injection devices 25 as the injection device 25 advances towards the base 16 of the apparatus. As used herein, a "lumen" is a cavity or inner open space of a tube which can be provided by a syringe or needle. A lumen for delivery of a treatment substance may be within a needle, or between a needle and an outer guide or sleeve. Multiple lumens may be formed within a single needle, with the outlet ports positioned on different locations on the needle.

Figure 7:
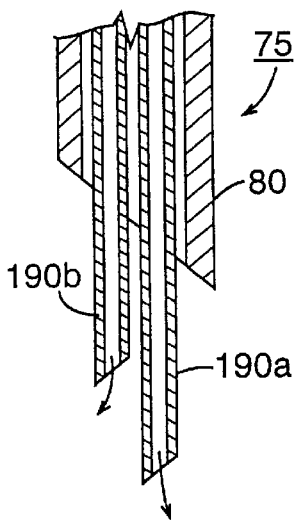
FIG. 7 is an enlarged partial sectional view of an alternative embodiment of a multi-site injection device via two separate needles according to the present invention.

Each of the plurality of injection devices 25 have opposing first and second ends 26, 27. The devices 25 have a first extended position and a second retracted position. As shown in FIG. 4, upon extension of the injection device 25, the first end 26 is configured to contact and rest against predetermined areas of the external egg shell. As shown in FIG. 1, when not injecting, the injection devices 25 are retracted to rest a predetermined distance above the eggs and stationary base 16. Alternatively, the base 16 can be longitudinally slidably moveable to position the eggs in proper position relative to the injection delivery device 25 (not shown). For ease of discussion, the description describes a unit with a single multi-site injection device 25 (shown as a top injection device) but the description also applies to an apparatus with multiple injection devices 25', 25" (exemplarly shown in FIGS. 10 and 11), or, alternatively, one or more of single bottom or side devices. For ease of illustration, FIG. 3 shows a single needle device, essentially the same as the device currently marketed by Embrex Inc., but with the fluid supply altered so that a second treatment substance rather than a disinfectant solution is channeled through the lumen between the needle and the outer guide. However, a dual needle device, such as is shown in FIG. 7, is currently preferred so that the outer lumen remains available for a cleansing solution.

In an alternate embodiment of FIG. 3, a single needle device may be employed, and suitable valves and controls used (not illustrated) so that a treatment solution passes through the outer lumen and is administered into the egg while the device is inserted into the egg, and a cleansing solution passes through the outer lumen and cleanses the needle while the device is withdrawn from the egg, and prior to insertion into the next egg for delivery.

Figure 13:
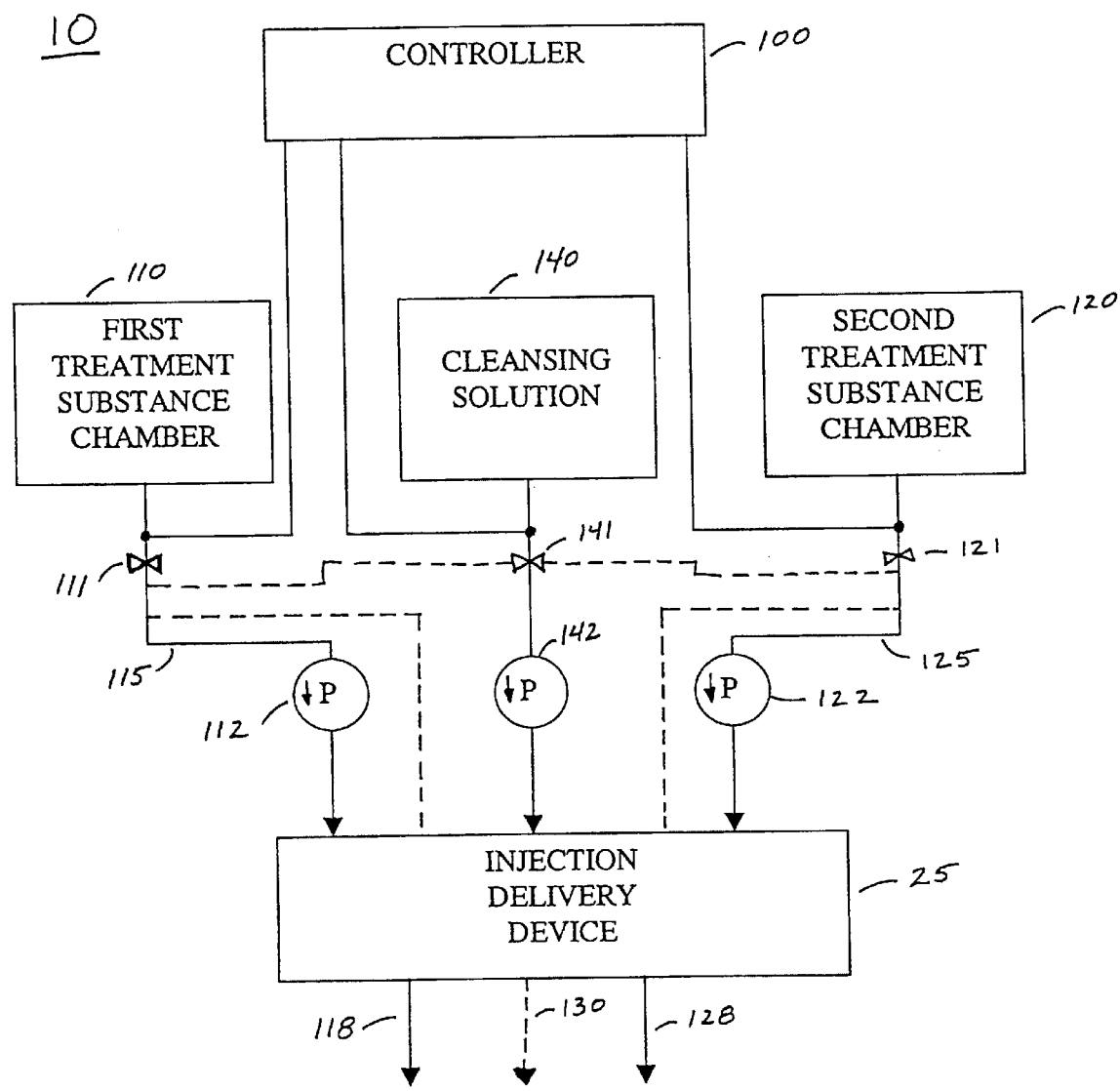
FIG. 13 is a block diagram of an apparatus according to the present invention showing two separate treatment chambers, a separate cleaning solution chamber, and a controller, along with corresponding pumps and valves and separate injection paths; further, and optionally, the dotted lines illustrate the delivery of the separate treatment substances along a common delivery path.

Preferably, as shown in FIG. 3, the second end 27 of the injection delivery device includes first and second inlet ports 28a, 28b which are configured to receive first and second tubing 30, 31 respectively. The first and second tubing are in fluid communication with first and second treatment substance chambers 110, 120 (FIG. 13). In order to maintain the separate delivery paths 60, 61 of the treatment substances through the injection device 25, the injection devices 25 preferably include a first and second passage (not shown) formed therein which are in fluid communication with the first and second inlet ports 28a, 28b, respectively, as would be understood by one skilled in the art. In one embodiment of the present invention, as shown in FIGS. 3 and 4, the delivery paths 60, 61 are maintained separate from the other even when the lumens or needle(s) are injected into the egg. Alternatively, the delivery paths 60, 61 can merge immediately or a short time prior to delivery into the egg.

As shown in FIG. 3, A multi-site in ovo injection head 25 for delivering compounds inside an egg comprises a body member 40 having opposing top 43 and bottom 41 end portions and an elongate longitudinal aperture formed therein; and a delivery device positioned in said aperture. The delivery device has at least two lumens formed therein (in the case where the lumen between the guide and the inner needle is used to carry compound to be introduced into the egg, the guide itself being considered a portion of the delivery device). In a preferred embodiment as illustrated in FIG. 7, the drug delivery device comprises a first needle and a second needle, each of the needles containing one of said lumens. Also preferably, the first and second needles are configured to deliver substances through the lumens thereof to spatially separate locations within an egg to be injected. The device includes an egg locating member, or egg engaging member 26, connected to the body member bottom end portion, which as illustrated is slidably connected to the body member and includes a spring 42 to both cushion the engagement, and hold the egg in place during the downstroke of the injection head. As illustrated, an outer guide 80 is provided to pierce the egg shell, and the needle 60 then extends beyond the outer guide and into the desired compartments of the egg (see FIG. 4). The device illustrated in FIG. 3 is commercially available from Embrex Inc. in a single needle embodiment (where a chlorine cleansing solution only passes through the outer lumen), but not as a dual needle embodiment as illustrated in FIG. 7.

The dual needle embodiment of FIG. 7 is currently preferred because the outer lumen 61 (see FIGS. 5 and 6) then remains available for a sanitizing or disinfecting solution. Where a dual needle embodiment is used, the inlet head 43 is modified to incorporate additional ports for introduction of additional compounds.

As shown by the block diagram in FIG. 13, the apparatus 10 preferably includes a main controller 100, first and second treatment substance chambers 110, 120, associated valves 111, 121 and one or more drive means such as pumps 112, 122 operably associated with the substance chambers for delivering the appropriate amounts of treatment substances to the injection delivery device 25. Although the apparatus 10 is illustrated as having a separate drive means for each fluid or treatment chamber 110, 120, it will be appreciated by one of skill in the art that the invention is not limited thereto. Indeed, a single electric or pneumatic pump can be connected to each substance chamber to deliver each treatment substance to the inlet ports 30, 31 in the injection device. Preferably, the apparatus 10 incorporates one or more high speed peristaltic pumps or solenoid activated pumps, actuated to deliver precise dosages of treatment substances to the injection devices and ultimately to the egg. One such peristaltic pump is described in U.S. patent application Ser. No. 08/926,160 of Fenstermacher and Hall, filed Sep. 9, 1997, the contents of which is incorporated herein as if recited in its entirety.

Optionally, as illustrated by the dotted line paths in FIG. 13, the apparatus 10 can be configured to separately store the treatment substances in the respective chambers 110, 120 and then channel them through a single lumen for delivery into the egg. A valve, controlled by the controller, is required to alternately switch from one treatment fluid source to the other. Switching is timed with positioning of the needle so that different fluids are injected in different compartments within the egg. The different treatment substances can each be provided in liquid, solid, gas or aerosol form, or any other suitable form, so long as the substances are substantially separated from one another (e.g., liquid treatment substances separated by an intervening gas bubble) so that different treatment substances are placed in different compartments.

Also preferably, as also shown in FIG. 13, the apparatus 10 includes a cleaning solution chamber 140 operably associated with the controller 100 and plumbed to be in fluid communication with each of the separate substance delivery channels 115, 125 upstream of the injection delivery device 25 as well as the one or more fluid or substance delivery paths 118, 128 (130) in the injection device itself 25. This will allow the delivery paths 118, 128 (130) to be flushed with a decontamination fluid to maintain a preferred level of sterility in the apparatus so as to reduce the likelihood of cross-contamination between eggs or the growth of undesired contaminants in the delivery paths to help maintain the apparatus in optimum performance condition. Any conventional cleansing solution may be used, with chlorine cleansing solutions preferred.

In operation, in one embodiment of the present invention, a controller 100 directs the opening of the valves 111, 121 to release predetermined dosages of treatment substance into first and second tubes 30, 31. The associated drive means or pumps 112, 122 forces the substances into delivery paths 115, 125 (such as through tubing 30, 31) in fluid communication with each of the injection delivery devices 25 via inlet ports thereon 28a, 28b.

In order to inject the shell with the desired treatment substances, as illustrated by FIGS. 3 and 4, the apparatus 10 preferably includes a shell piercing means such as an outer guide punch 80 which punctures at least one small opening into the outer shell of an egg. Alternatively, a high pressure water jet can also be employed. The outer guide punch 80 is preferably formed from a durable and rigid material, or the needle or injection device itself can serve as the shell piercing means. Advantageously, configuring the outer guide punch 80 to pierce the shell of the egg will help preserve the life of the needle(s) 90 as the needle(s) 90 can be inserted into the opening formed by the punch 80 and will not have to pierce the shell before entry into the egg.

Also, as shown in FIG. 4, the outer guide punch 80 preferably does not advance into the inner shell membrane. The needle(s) can be formed of any suitable material such as but not limited to stainless steel or plastic. If formed of plastic, a compatible epoxy can be employed to assemble in position in the hub assembly 40. The egg inserting ends of the needle(s) 90 are preferably sufficiently sharp to be able to pierce the inner shell membrane or chorioallantois with minimum tearing attributed thereto. Alternatively, blunt, dull, or side-port needles can be employed, particularly where it is desired that the needle avoid piercing a particular underlying membrane or the embryo proper.

Figure 8:
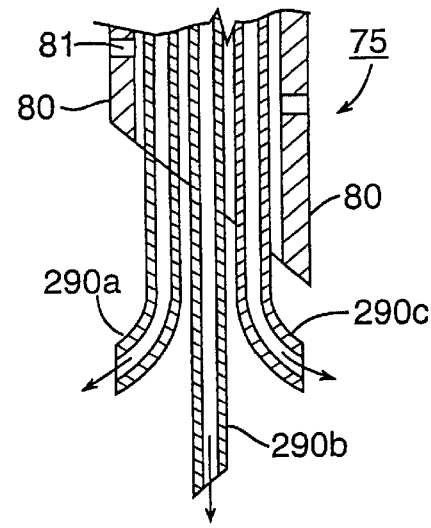
FIG. 8 is an enlarged partial sectional view of another embodiment of a multi-site injection device via three separate needles.

In operation, the outer guide 80 preferably advances a predetermined short distance into the egg. The injection device 25 then extends the lumens or needle(s) 90 into the egg through the preformed opening. The needles 90 are configured to release (preferably simultaneously) a predetermined dosage of the substances into predetermined sites, such as above or below the air cell and into the amnion of the avian embryo (as will be discussed in more detail hereinbelow). The needle(s) 90 are then retracted into the outer guide punch 80 and the guide punch 80 is returned to the stationary storage position within the bottom portion of the injection device 26 and, as described above, the entire injection unit is then retracted and preferably flushed before the next flat of eggs are advanced. Preferably, the exterior surface of the needles and/or lumens are then flushed to disinfect or clean the injection device 25 such that remnants of the injected egg or other contaminants are flushed out of the delivery paths 60, 61 and the exterior portion of the needle tip(s) are sanitized. In a preferred embodiment, as illustrated in FIG. 8, the outer guide punch 80 includes a plurality of apertures 81 formed therearound to allow the cleaning solution to flush the exterior surface as well as the interior lumens.

Turning back to FIG. 4, the injection delivery device 25 is shown in a preferred position in the egg, i.e., one lumen 61 delivering a first substance in the air cell and the other lumen 60 extending farther down to deliver a second substance below the chorioallantois membrane. As shown in FIG. 5, the outer guide punch 80 defines the second delivery path 61 (one lumen) and a needle 90 held with the inner diameter of the guide punch 80 defines the first delivery path 60 (a second lumen). The needle 90 may include a curved end 92 to direct the substance in a predetermined direction when released into the egg. This configuration can provide further separation of treatment materials when released within the egg. FIG. 6 illustrates the separate delivery paths (exemplarly shown as concentric lumens) of the materials within the injection head 75.

FIGS. 7 to 12 illustrate alternative configurations of an injection head 75 that provide alternative substance delivery paths into the egg. In a particularly preferred embodiment, FIG. 7 shows two separately extending needles 190a, 190b, one extendable a predetermined further length than the other. The outer guide punch 80 can provide a separate lumen or delivery path, but is preferably used to provide an outlet for a sanitizing fluid or cleansing fluid. For a third treatment substance, as noted above, FIG. 8 illustrates three needles, a central needle 290b and two side needles 290a, 290c. As illustrated, the central needle 290b extends a further distance than the side needles 290a, 290c. The side needles 290a, 290c may be curved to direct the treatment substances away from the central needle 290b and the other opposing side needle. Alternatively, one or more of the needles can be a side port needle which can direct the substance in an angular trajectory path relative to the longitudinal extension of the needle.

Figure 9:
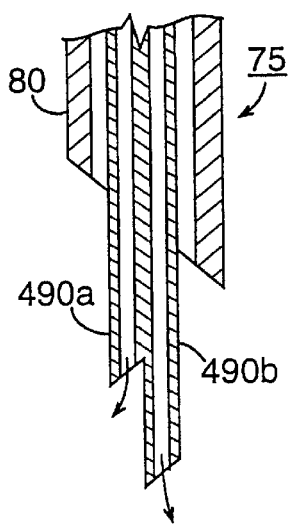
FIG. 9 is an enlarged partial sectional view of another embodiment of a multi-site injection device via two joined needles.
Figure 10:
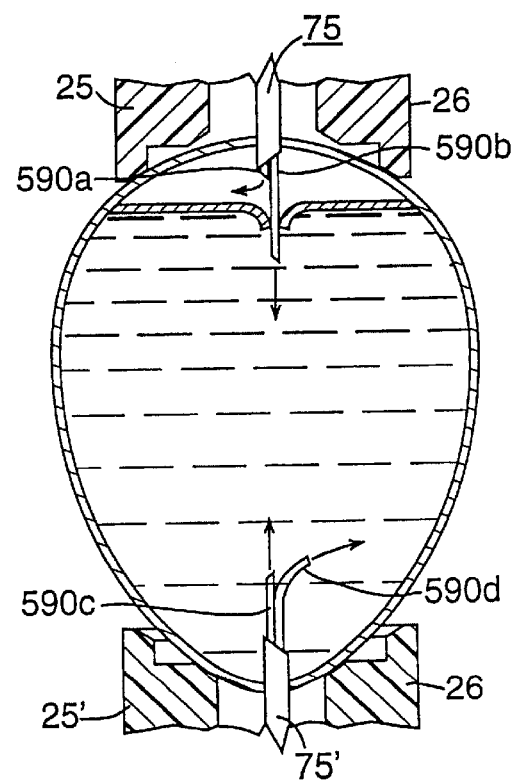
FIG. 10 is an enlarged partial sectional view of dual injection head multi-site injection device and another embodiment of treatment delivery needles and associated delivery paths into an egg.
Figures 11, 12:
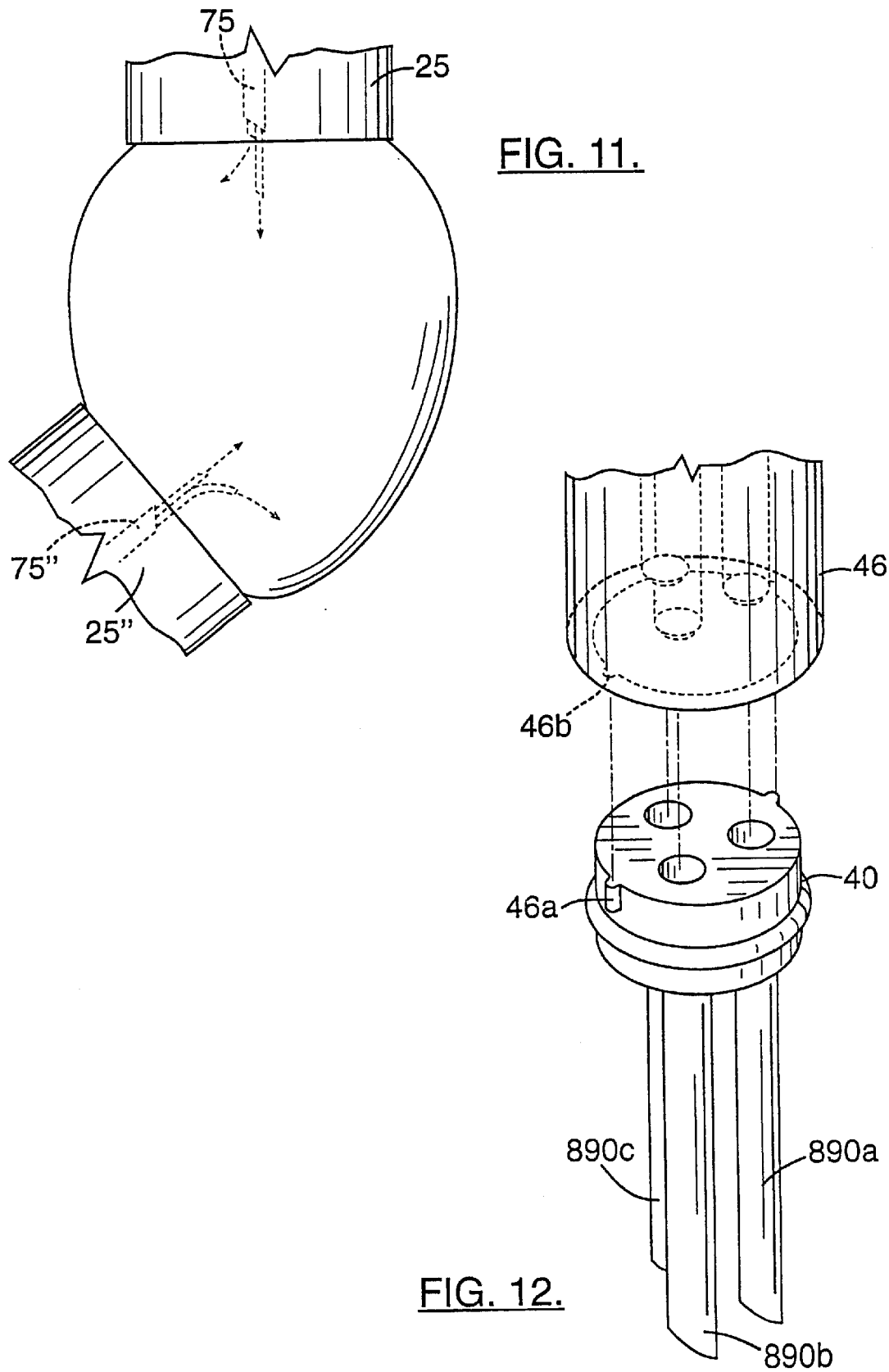
FIG. 11 is an enlarged partial sectional view of an alternative embodiment of a dual injection head multi-site injection device and further illustrating alternative substance delivery paths into an egg.
FIG. 12 is a partial exploded view of a needle hub configured to be interchangeably and alignably assembled to the multi-site injection head.

FIG. 9 illustrates two needles 490a, 490b structurally joined a major distance of the length of the needles. Alternatively, a single needle or device with multiple lumens could be used. FIG. 10 shows a top and bottom multi-site injection delivery device 75, 75' each having alternatively configured needles 590a, 590b, 590c, 590d for directing the substance in a desired area of the developing egg. Similarly, FIG. 11 illustrates a side and top multi-site injection delivery device 75, 75". Note that where two (or more) holes are made in the egg shell, particularly in a configuration that would cause the contents of the shell to drain from the egg, then at least one of the holes (preferably the lower hole) should be sealed, in accordance with known techniques, to prevent draining of the egg.

Alternatively, an injection delivery device may have a needle with two lumens that terminate into a single lumen at a position prior to the end of the needle. This configuration keeps the substances separate a major portion of the substance delivery path but allows them to mix at the site of injection.

The apparatus of the instant invention can also employ a side or bottom injection device 25', 25". One or more of these alternative injection devices can be used concurrently with a top injecting device or subsequent or prior in time. Of course the flat must be altered to provide access to the appropriate part of the egg shell. When injecting from the bottom, it is preferred to position the bottom injection device opposing the top injection device and further preferred to configure the injection head 75 and depth of injection to inject into the yolk sac. Note that when injecting into the yolk sac a small needle such as a 25 gauge needle is preferred in order to reduce the risk of yolk sac leaks. When injecting from the side it is preferred that the needles be inserted at an angle below 90E with respect to a plane normal to the longitudinal axis of the egg. As shown in FIG. 11, it is more preferred that the side injection head 75" be positioned and configured to enter the egg at about 45 degrees or less relative to the longitudinal axis of the egg.

FIG. 12 illustrated an interchangeable needle hub 33 having a plurality of needles 890a, 890b, 890c. The needle hub 33 is provided with an alignment tab 33a that is configured to matingly engage a complimentary-shaped detent 46b in the illustrated injection head 46. Accordingly, the needle hub 33 can be alignably assembled to the injection head 46.

In two preferred embodiments as illustrated in FIGS. 7 and 8, the injection head 75 includes a 16 gauge outer guide punch 80 which surrounds two or three 25 gauge needles therein.

Treatment substances may administered as a bolus in the same or different physical form, such as liquid, gas, solid (e.g., a powder or a unitary erodable time-release matrix), aerosol or spray, etc.

The bolus of treatment substance may be administered into any suitable compartment of the egg, including intraperitioneally, intramuscularly, or subcutaneously within the embryo, into the yolk sac or stalk, into the liver or lungs of the embryo, into the air cell, the allantoic sac, or the amniotic fluid, etc. In some cases it may be desireable to administer two different substances into different locations within the same compartment (e.g., intraperitoneal or intramuscularly, or even into the amniotic fluid for rapidly absorbed but otherwise incompatible treatment substances). In addition, it may be desireable in some cases for the first and second treatment substances to be the same, but simply administered in different locations within the egg.

Treatment substances that may be administered include, but are not limited to, vaccines, hormones, growth-promoting agents, etc.

In one preferred embodiment, one of the treatment substances is Newcastle's disease vaccine, and the other treatment substance is Marek's disease vaccine. Marek's disease vaccine is preferably administered into the region defined by the amnion; Newcastle's disease vaccine is preferably administered into the air cell.

In another preferred embodiment, one of the treatment substances is a biologically active substance such as a vaccine, antibiotic, hormone, probiological culture (e.g., a competitive exclusion media), and the other is a marker such as a dye. The marker can serve as a positive control to confirm injection, for example in the case of eggs subsequently found to be nonviable.

Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A method for treating avian embryos in ovo, comprising the steps of: orienting an avian egg into a predetermined position; introducing a small first opening into the shell of said egg;

extending a delivery device through the first opening and into the egg a predetermined depth;

releasing a predetermined dosage of a substance into a first location of the egg;

removing a sample from a separate second location of the egg; and retracting the delivery device from said egg, thereby treating said avian embryo.

2. A method according to claim 1, wherein the delivery device includes first and second needles, and wherein the first needle extends longitudinally farther into said egg than the second needle.

3. A method according to claim 1, wherein the first and second locations are different compartments of said egg.

4. A method according to claim 1, further comprising the steps of:
introducing a second opening into the egg shell separate from the first opening and extending a second delivery device therethrough; and
releasing a predetermined dosage of a second substance into a third location of the egg and removing a sample from a separate fourth location of the egg.

5. A method according to claim 4, wherein at least one substance is introduced via the first delivery device above the air cell and another substance is introduced via the second delivery device into the yolk sac, allantois, amnion or embryo.

6. A method according to claim 1, wherein said delivery device has a first lumen formed therein, wherein said substance is delivered through said first lumen, and wherein said sample is removed through said first lumen.

7. A method according to claim 1, wherein the opening is introduced by piercing the shell with a guide.

8. A method according to claim 1, further comprising the step of flushing the delivery device with a cleansing solution after delivery of the substance into the egg and after removal of the sample from the egg.

9. A method according to claim 1, wherein delivery of the substance and removal of the sample occurs substantially simultaneously in time.

10. A method according to claim 1, wherein delivery of the substance and removal of the sample occurs sequentially in time.

11. A method according to claim 1 wherein said sample is a liquid sample.

12. A method for removing samples from avian embryos in ovo, comprising the steps of:
orienting an avian egg into a predetermined position;
introducing a small first opening into the shell of said egg;
extending a sample removal device through the first opening and into the egg a predetermined depth;
removing first and second samples from the egg in respective first and second separate locations therein; and
retracting the sample removal device from said egg.

13. A method according to claim 12, wherein the sample removal device includes first and second needles, and wherein the first needle extends longitudinally farther into said egg than the second needle.

14. A method according to claim 12, wherein the first and second samples are removed from different compartments of said egg.

15. A method according to claim 12, further comprising the steps of introducing a second opening into the egg shell separate from the first opening and extending a second sample removal device therethrough.

16. A method according to claim 15, wherein at least one sample is removed via the first sample removal device above the air cell and another substance is introduced via the second sample removal device from the yolk sac, allantois, amnion or embryo.

17. A method according to claim 12, wherein said sample removal device has a first lumen formed therein, and said first and second samples are both removed through said first lumen.

18. A method according to claim 12, wherein the opening is introduced by piercing the shell with a guide.

19. A method according to claim 12, further comprising the step of flushing the sample removal device with a cleansing solution after removal of the first and second samples from the egg.

20. A method according to claim 12, wherein the first and second samples are removed from the egg substantially simultaneously in time.

21. A method according to claim 12, wherein the first and second samples are removed from the egg sequentially in time.

22. A method for treating avian embryos in ovo, comprising the steps of: orienting an avian egg into a predetermined position; introducing a small first opening into the shell of an avian egg;
introducing a small second opening into the shell of an avian egg, the second opening being spaced apart from the first opening;
extending a delivery device through said first opening into the egg a predetermined depth and to a first location within said egg;
extending a sample removal device through said second opening into the egg a predetermined depth and to a second location within said egg different from said first location;
releasing a predetermined dosage of a substance from said delivery device into said egg;
removing a sample from said egg second location via said sample removal device; and
retracting the delivery device and sample removal device from said egg, thereby treating the avian embryo.

23. A method according to claim 22, wherein the delivery device comprises an outer guide member and a plurality of needles enclosed therein, said method further comprising the step of downwardly extending the needles thereby puncturing the membrane of the egg before releasing the substance thereto.

24. A method according to claim 23, wherein the sample removal device is upwardly extended to remove said sample from within or adjacent the albumen, the yolk sac, embryo, allantois, or amnion.

25. A method according to claim 24, wherein delivery of the substance and removal of the sample occurs substantially simultaneously in time.

26. A method according to claim 24, wherein delivery of the substance and removal of the sample occurs sequentially in time.

27. A method for removing samples from avian embryos in ovo, comprising the steps of:
orienting an avian egg into a predetermined position;
introducing a small first opening into the shell of an avian egg;
introducing a small second opening into the shell of an avian egg, the second opening being spaced apart from the first opening;
extending a first removal device through said first opening into the egg a predetermined depth and to a first location within said egg;
extending a second removal device through said second opening into the egg a predetermined depth and to a second location within said egg different from said first location;
removing a first sample from said first location;
removing a second sample from said second location; and retracting the first and second sample removal devices from said egg.

28. A method according to claim 27, wherein the first removal device comprises an outer guide member and a plurality of needles enclosed therein, said method further comprising the step of downwardly extending the needles thereby puncturing the membrane of the egg before removing the first sample therefrom.

29. A method according to claim 28, wherein the second removal device is upwardly extended to remove the second sample from within or adjacent the albumen, the yolk sac, embryo, allantois, or amnion.

30. A method according to claim 29, wherein the first and second samples are removed substantially simultaneously in time.

31. A method according to claim 29, wherein the first and second samples are removed sequentially in time.

32. An automated in ovo injection apparatus, comprising:
a flat for holding a plurality of eggs in a substantially upright and aligned position, wherein said flat is configured to provide external access to predetermined areas of the eggs;
a plurality of injection delivery devices configured to contact predetermined areas of said egg, at least one of said injection devices corresponding to each egg in said flat, each of said delivery devices including first and second lumens adapted to be received into said egg;
a first container for holding a treatment substance, said first container in fluid communication with each of said first lumens;
a second container for receiving a sample from each egg, said second container in fluid communication with each of said second lumens;
at least one pump operably associated with said first and second containers and said injection devices and configured for delivering a predetermined dosage of said treatment substance to each of said first lumens and for removing a sample from each egg via each of the second lumens.

33. An automated injection apparatus according to claim 32, wherein said first and second lumens are defined by first and second needles concentrically disposed with respect to each other.

34. An automated injection apparatus according to claim 33, wherein one of said first and second needles is telescopically extendable a further distance than the other.

35. An automated injection apparatus according to claim 32, wherein said first and second lumens are defined by first and second needles adjacently disposed with respect to each other and wherein one of said first and second needles is longitudinally extendable a further distance relative to the other.

36. An automated injection apparatus according to claim 32, wherein each of said injection delivery devices further comprise:
an outer guide punch having opposing first and second ends and defining a cylindrical passage therebetween;
a plurality of needles contained within said outer guide passage and extendable in a longitudinal direction from said outer guide first end, said needles having a retracted position and an extended position, wherein in said retracted position said needles are contained within the second end of said outer guide, and in said extended position at least one of said plurality of needles extends beyond said outer guide second end.

37. An automated injection apparatus according to claim 36, wherein said plurality of needles includes a first and second needle positioned within said outer guide, and wherein said first needle is longitudinally extendable a greater distance into said egg relative to said second needle.

38. An automated injection apparatus according to claim 36, wherein said outer guide includes a plurality of apertures thereon, thereby allowing cleaning substances to be flushed therethrough.

39. An automated injection apparatus according to claim 32, wherein said at least one injection device corresponding to each egg includes first and second injection devices corresponding to each egg in said flat.

40. An automated injection apparatus according to claim 39, wherein said first injection device is configured to inject the top large end of the egg and the second injection device is configured to inject into a separate opening spaced apart from said first injection device.

* * * * *